(12) United States Patent
Sondermann et al.

(10) Patent No.: US 10,322,031 B2
(45) Date of Patent: *Jun. 18, 2019

(54) OPHTHALMOLOGICAL DEVICE

(71) Applicant: Carl Zeiss Meditec AG, Jena (DE)

(72) Inventors: Mario Sondermann, Quohren (DE);
Marco Hanft, Jena (DE); Dirk Doering, Erfurt (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,167

(22) Filed: May 8, 2018

(65) Prior Publication Data

US 2018/0325727 A1 Nov. 15, 2018

Related U.S. Application Data

(63) Continuation of application No. 15/415,353, filed on Jan. 25, 2017, now Pat. No. 10,004,641, which is a
(Continued)

(30) Foreign Application Priority Data

Mar. 25, 2011 (DE) .................. 10 2011 006 085

(51) Int. Cl.
*A61F 9/08* (2006.01)
*A61B 3/10* (2006.01)
(Continued)

(52) U.S. Cl.
CPC ............ *A61F 9/009* (2013.01); *A61B 3/0008* (2013.01); *A61B 3/10* (2013.01); *A61B 3/1173* (2013.01);
(Continued)

(58) Field of Classification Search
CPC .. A61F 9/009; A61F 9/00804; A61F 9/00827; A61F 2009/0087;
(Continued)

(56) References Cited

U.S. PATENT DOCUMENTS 6,741,359 B2 5/2004 Wei et al.
8,235,973 B2 8/2012 Vogler et al.
(Continued)

FOREIGN PATENT DOCUMENTS

DE 10 2005 013 949 A1 9/2006
DE 10 2008 027 358 A1 12/2009
(Continued)

OTHER PUBLICATIONS

Glasser et al., "Biometric, optical and physical changes in the isolated human crystalline lens with age in relation to presbyopia," Vision Research, 39 (1999), pp. 1991-2015.
(Continued)

*Primary Examiner* — Scott Luan
(74) *Attorney, Agent, or Firm* — Patterson Thuente Pedersen, P.A.

(57) ABSTRACT

An ophthalmic instrument for the application of laser radiation in a patient's eye, particularly for the examination and/or surgical laser treatment of the cornea and the lens of the eye, includes a femtosecond laser, an objective and optical assemblies. The optical assemblies are arranged in front of the objective, and selectively vary the focus position in the coordinate direction X, Y and Z either within the region of the cornea or within the region of the lens of the eye. The objective or at least one lens group is movable relative to the eye. The variation of the position of the lens group objective shifts the focus position from the cornea to the lens of the eye and vice versa.

11 Claims, 3 Drawing Sheets

Related U.S. Application Data continuation of application No. 14/006,017, filed as application No. PCT/EP2012/050035 on Jan. 3, 2012, now Pat. No. 9,554,943.

(60) Provisional application No. 61/467,712, filed on Mar. 25, 2011.

(51) Int. Cl.
*A61B 3/00* (2006.01)
*A61B 3/117* (2006.01)
*A61F 9/009* (2006.01)
*A61F 9/008* (2006.01)
*A61B 3/107* (2006.01)

(52) U.S. Cl.
CPC ...... *A61F 9/00802* (2013.01); *A61F 9/00804* (2013.01); *A61F 9/00825* (2013.01); *A61F 9/00827* (2013.01); *A61B 3/107* (2013.01); *A61F 2009/0087* (2013.01); *A61F 2009/00844* (2013.01); *A61F 2009/00872* (2013.01); *A61F 2009/00897* (2013.01)

(58) Field of Classification Search
CPC .. A61F 2009/00897; A61F 2009/00844; A61F 9/008; A61B 3/11173; A61B 3/10
See application file for complete search history.

(56) References Cited

U.S. PATENT DOCUMENTS 8,702,770 B2   4/2014   Hanft et al.
2009/0299347 A1*  12/2009  Vogler .................. A61F 9/008 606/5
2010/0274228 A1   10/2010  Mrochen et al.
2011/0028948 A1   2/2011   Raksi et al.
2011/0028951 A1   2/2011   Raksi et al.

FOREIGN PATENT DOCUMENTS

| DE | 11 2008 002 511 T5 | 7/2010 |
| DE | 10 2009 012 873 A1 | 9/2010 |
| JP | 2008-534993 A | 8/2008 |
| JP | 2009-279398 A | 12/2009 |
| WO | WO 2008/087483 A1 | 7/2008 |
| WO | WO 2010/142311 A1 | 12/2010 |
| WO | WO 2011/011202 A1 | 1/2011 |

OTHER PUBLICATIONS

Mashige, "A review of corneal diameter, curvature and thickness values and influencing factors," The South African Optometrist, 2013, 73(4) 185-194.

Japanese Office Action for Japanese Application No. 2016-176118, dated Jul. 18, 2017, 7 pages (Japanese and English language versions).

Japanese and English Language Japanese Office Action for Japanese Application No. 2014-5002914, dated Nov. 4, 2015, 9 pages.

Application and File History for U.S. Appl. No. 14/006,017, filed Nov. 26, 2013. Inventors: Mario Sondermann et al.

Application and File History for U.S. Appl. No. 15/415,353, filed Jan. 25, 2017. Inventors: Mario Sondermann et al.

* cited by examiner

OPHTHALMOLOGICAL DEVICE

RELATED APPLICATIONS

The present application is a continuation of U.S. application Ser. No. 15/415,353, filed Jan. 25, 2017, entitled "Ophthalmological Device," which is a continuation of U.S. application Ser. No. 14/006,017, filed Nov. 26, 2013, now U.S. Pat. No. 9,554,943, issued Jan. 31, 2017, entitled "Ophthalmological Device," which is a National Phase entry of PCT Application No. PCT/EP2012/050035, filed Jan. 3, 2012, which claims priority to DE Application No. 102011006085.5, filed Mar. 25, 2011, and U.S. Provisional Patent Application No. 61/467,712, filed Mar. 25, 2011, which applications are incorporated by reference herein in their entirety.

FIELD OF THE INVENTION

The present invention relates to an ophthalmic instrument for the use of laser radiation on and in the eye, especially for the examination and/or surgical laser treatment of the cornea and the lens of the eye.

BACKGROUND

Ophthalmic instruments are used, for example, to correct an ametropia of the human eye by means of a surgical laser operation on the cornea. A method of particular importance is known as "LASIK" (laser in-situ keratomileusis), in which, by application of a pulsed laser beam, material is ablated from inside the cornea rather than from its surface. For this purpose, a flap is formed on the outer corneal surface, the thickness of this flap being substantially smaller than the thickness of the cornea. For the ablation treatment proper, the flap is folded back, whereupon a pulsed laser beam is used to ablate material from the exposed area to correct the ametropia. Thereafter, the flap is closed again onto the treated surface.

To form the flap at a precisely defined depth of the cornea and as gently and precisely as possible, it has been suggested to use femtosecond laser pulses, i.e. laser pulses having pulse widths smaller than $10^{-12}$ s. By application of such pulses it is possible to create localized optical ruptures in the cornea, known as photodisruptions, the size of which is limited to a few micrometers. By positioning a dense array of many such disruptions in exactly defined places, the flap can be made to measure very precisely. For the precise forming of the flap it is essential that the focus of the pulsed laser beam is exactly positioned not only laterally but also, and mainly so, in the depth of the cornea, i.e. in the propagation direction of the laser beam.

In this connection, DE 10 2005 013 949 A1 describes a scanning device for, and a method of, focusing a beam of rays into a given volume. This scanning device is especially suitable for use in instruments intended for surgical laser treatment of the cornea with laser radiation pulsed in the femtosecond range. The device allows the laser light to be focused on any target points within the cornea.

DE 10 2008 027 358 A1 describes a laser system that can be used in ophthalmic instruments for the analysis and treatment of the lens of the eye. Other than laser systems in comparable instruments, it has the advantage that the detection of the laser light backscattered in the lens of the eye is possible with greater accuracy, so that a refractive surgical therapy of the lens of the eye can be performed with higher precision. For this therapy, laser radiation pulsed in the femtosecond range is focused on selected target points within the lens of the eye.

The state of prior art described above regarding the medical examination and surgical laser treatment of the cornea (situated at the periphery of the eye) on the one hand and the lens (situated within the eye) on the other has the disadvantage that the ophthalmic instruments available satisfy the requirements of one of these special applications only; i.e., they differ with regard to their imaging properties, in particular: to their aperture, focal spot size, focus position in the eye, correction of the aperture aberration or correction of field aberrations to such an extent that they are exclusively suitable either for the examination and treatment of the cornea or for the examination and treatment of the lens of the eye.

This means that an oculist needs to procure two instruments, which is inefficient (a) with regard to acquisition cost and (b) because several single-purpose instruments are seldom used to capacity. In addition, separate instruments involve extra time for getting adjusted at least to the same eye of a patient being examined.

SUMMARY OF THE INVENTION

Departing from this, the invention is based on the problem of creating an ophthalmic instrument that can be used for the examination and surgical laser treatment of both the cornea and the lens of the eye.

According to the invention, this problem is solved by an ophthalmic instrument of the kind described above, which comprises:

a femtosecond laser as a source of laser radiation, an objective from which laser radiation emerges that is focused in the direction of the patient's eye, optical assemblies which are arranged upstream of the objective, and which are, in operative connection with the objective, intended for varying the focus position in the coordinate direction X, Y and Z, selectively either within the region of the cornea or within the region of the lens of the eye, with the objective itself being movable relative to the eye or at least having one lens group whose position is movable relative to the eye, the variation of the objective or lens group position being intended to shift the focus position from the region of the cornea to the region of the lens of the eye and vice versa.

The distances are varied by shifting the respective lens groups of the objective along their optical axis. Besides the focus position, the variation of the distances also influences the correction of the imaging aberrations. Variation of the focus in depth causes changes, e.g., in spherical aberration, unless this is compensated by the lens movements.

Favorably, the lens groups of the objective can be displaced between two limit positions that define two different specified distances along the optical axis. One of these limit positions is assigned to the focus positioned in the region of the cornea, the other to the focus positioned in the region of the lens of the eye. In the sense of the invention, positioning the focus "in the region of the cornea" means that the focus can be directed at any target points on or in the cornea, while positioning the focus "in the region of the lens of the eye" means that the focus can be directed at any target points on or in the lens of the eye. For the purpose of shifting from one limit position to the other, the movable lens groups are preferably coupled with electromechanical drive units, which are connected to a control unit.

In principle, the shifting of lens groups of the objective corresponds to switching between two operating modes, with the instrument being available for the examination and treatment of the lens of the eye in one operating mode, and for the examination and treatment of the cornea in the other operating mode, which, in principle, solves the problem of the invention.

In an embodiment, an optical element of negative refractive power that can be moved in the direction of radiation is arranged upstream of the objective, that movement being used to vary the focus position in the coordinate direction Z, but only either within the region of the cornea or within the region of the lens of the eye. The moving of this element varies the divergence of the beam. Depending on the currently set divergence angle, the objective focuses the beam on various positions in Z direction—either within the region of the cornea or within the region of the lens of the eye.

The movable optical element may be configured, e.g., as a lens, a reflective or a diffractive optical element. Preferably, it is a lens. To permit its controlled movement along the optical axis, the lens moves in a straight-line guide that is aligned in parallel with the beam path.

Also arranged upstream of the objective, there is a device for deflecting the laser radiation in the X and Y coordinate directions, this lateral deflection also being possible only within either the region of the cornea or the region of the lens of the eye.

In principle, the deflecting device may be designed in a manner that is known per se. For example, it may merely consist of a mirror that is tiltable about two different, preferably orthogonal, axes. Preferably, though, it comprises two mirrors arranged at a distance from each other and oscillating relative to each other. This advantageous design permits the mirrors to be seated and adjusted and, thus, the focus to be positioned laterally, with very high precision, though by simple means.

Between the two mirrors, an optical pupil element may be arranged that images the first mirror onto the second one, which results in a defined pupil position. In a precisely working optical system, a defined, permanent position of the pupil is a prerequisite for good correction.

Between the deflecting device and the objective, a beamsplitter may be arranged, by which part of the observation light coming from the cornea or the lens of the eye is coupled out for observation or imaging purposes.

During the examination or treatment of the eye it is preferable to apply onto the cornea a contact glass with a concave contact surface in order to suppress eye movement. Moreover, the contact glass reduces the eye's refractive power and makes focus correction easier.

In an example embodiment of the invention, a collecting lens is arranged downstream of the movable lens of negative refractive power, so that both elements together form a beam expander assembly, which expands the diameter of a parallel beam incident to the lens by a specified amount. Thus, if a parallel beam having a diameter d1 enters the beam expander, the emerging parallel beam will have an exit diameter d2>d1.

The exit diameter has an influence on the aperture angle on the side of the patient's eye. This given, it is within the scope of the invention to provide structures for varying the aperture angle on the side of the patient's eye, e.g., several exchangeable negative lenses of varied divergence angles.

Exchanging the negative lenses for getting varied aperture angles on the side of the patient's eye can be done in connection with shifting the focus position from the region of the cornea to the region of the lens of the eye and vice versa, or else according to the size of the eye to be examined or treated, that size being defined preferably by the depth of the eye's anterior chamber. Such lens assemblies can be exchanged automatically or manually.

The instrument according to the invention can be used to advantage for fast and easy adjustment of the focus position in three dimensions within the region required, i.e. that of the cornea or that of the lens of the eye. There is no need any more to change from one instrument to another as in prior art.

BRIEF DESCRIPTION OF THE DRAWINGS

Subject matter hereof may be more completely understood in consideration of the following detailed description of various embodiments in connection with the accompanying figures. Below, the invention will be explained in greater detail with reference to exemplary embodiments. In the accompanying drawings.

Figure 1:
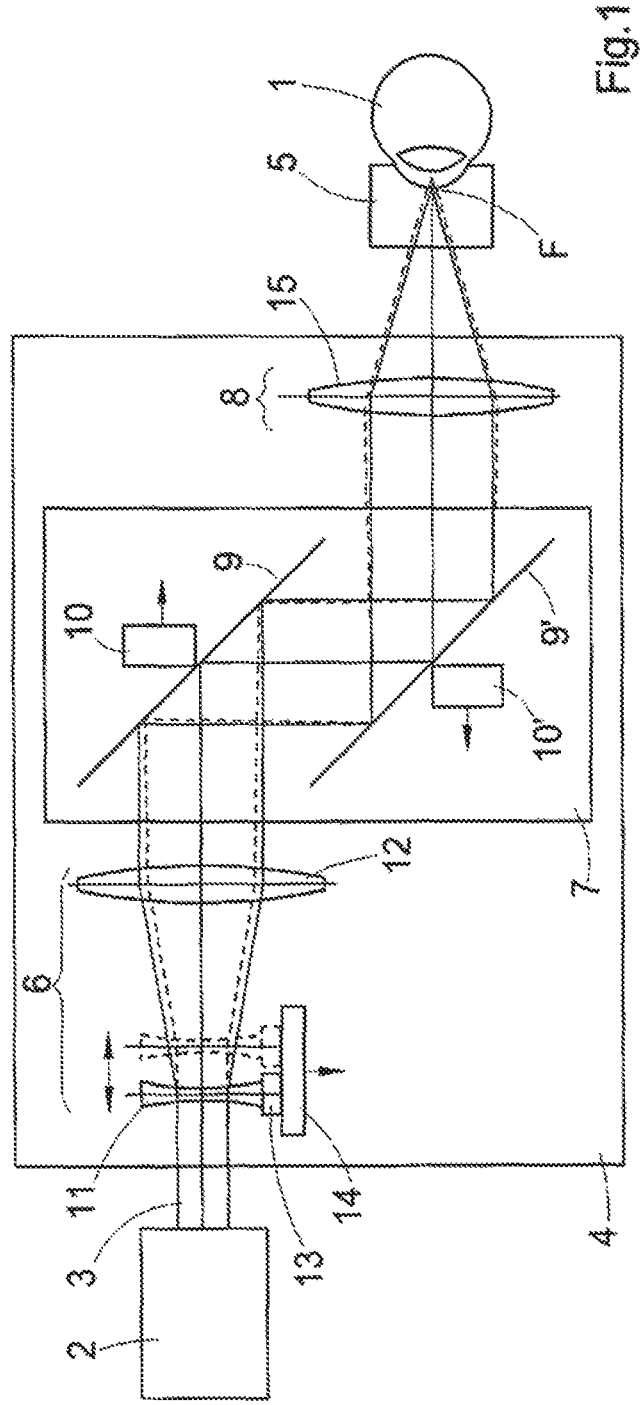
FIG. 1 is a schematic diagram of an ophthalmic instrument for the application of laser radiation according to prior art.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 shows an instrument for the treatment of a human eye 1 according to prior art. This instrument comprises a radiation source 2, which emits a beam 3 of laser radiation pulsed in the femtosecond range, and a scanning device 4, with which the beam 3 can be focused on selected positions within the region of the cornea. On the cornea there is a contact glass 5 having a concave contact surface, which suppresses movements of the eye 1 during examination or treatment.

The radiation source 2 is designed to emit, e.g., laser radiation in a wavelength range around 1040 nm with a pulse width of about 200 fs.

On its end facing the beam 3 emerging from the radiation source 2, the scanning device 4 features an optical entrance system 6. Next to this in the radiation direction, there is a deflecting device 7, which deflects the beam 3 emerging from the optical entrance system 6 laterally, i.e. in X and Y directions (across the Z direction of the incident beam 3) according to given control signals. Next to the deflecting device 7 in the beam path there is an objective 8, which focuses the beam 3 in the region of the cornea.

The deflecting device 7 is provided with two deflecting mirrors 9 and 9', which are mounted in bearings so as to be tiltable about axes not shown in FIG. 1. To simplify the diagram, the mirrors 9 and 9' in FIG. 1 are aligned in parallel; actually, however, the tilting axes are orthogonal to each other and to the optical axis of the optical entrance system 6, so that tilting the first mirror 9 deflects the beam 3 in Y direction, and tilting the second mirror 9' deflects it in the X direction orthogonal to the Y direction. The mirrors 9 and 9' are driven by actuators 10 and 10', respectively, which are connected to a control device via signal paths (indicated by arrows). According to the desired focus position in lateral direction, the control device sends control signals to the actuators 10 and 10', which then cause the mirrors 9 and 9' to tilt.

The optical entrance system 6 features a lens 11 of negative refractive power that is movable relative to the deflecting device 7, and a collecting lens 12. The lens 11 is connected with a straight-line guide 13, thanks to which it can be moved to vary the optically effective distance from the deflecting device 7. The movement of lens 11 in parallel to its optical axis can be effected, e.g., by means of a linear drive 14, which is also connected with the control device (which is not shown). According to the desired focus position in Z direction, the control device generates control signals sent to the linear drive 14.

The lens 11 and the collecting lens 12 are so designed that the optical entrance system 6 acts as a beam expander, which expands the diameter of the beam 3. Thus, if a parallel beam 3 with a diameter d1 enters the optical entrance system 6, a parallel beam 3 with a diameter d2>d1 will emerge from it.

The objective 8 is shown as a fixed lens 15; it focuses the beam 3 emerging from the optical entrance system 6 on a position in the region of the cornea, the position being defined by the lens 11 and the deflecting device 7.

The position of the focus F in the depth of the region of the cornea is defined by moving the 11 along its optical axis. The lateral position of the focus F is set by means of the deflecting device 7.

Figure 2:
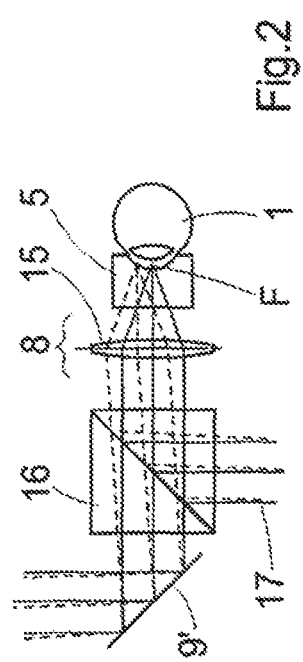
FIG. 2 depicts a variation of the arrangement shown in FIG. 1, featuring a beamsplitter for deflecting the observation beam towards a viewing tube with an eyepiece, or towards a camera.

FIG. 2 shows a variation of the arrangement shown in FIG. 1, with a beamsplitter 16 arranged in the beam path between the deflecting device 7 and the objective 8. By means of the beamsplitter 16, part of the light coming from the cornea and shaped by the objective 8 into an observation beam 17 is coupled out and deflected towards a viewing tube (not shown) with an eyepiece, or towards a camera (not shown either), so that the cornea can be observed during examination or treatment.

Further details of this state of prior art can be found in DE 10 2005 013 949 A1. Deviating from prior art, the problem of the invention is solved in such a way that the objective 8 consists of several lens groups and is designed to allow itself or at least one lens group to be moved relative to the eye, so that the distance variation effects a shifting of the focus position from the region of the cornea to the region of the lens of the eye and vice versa.

Figure 3:
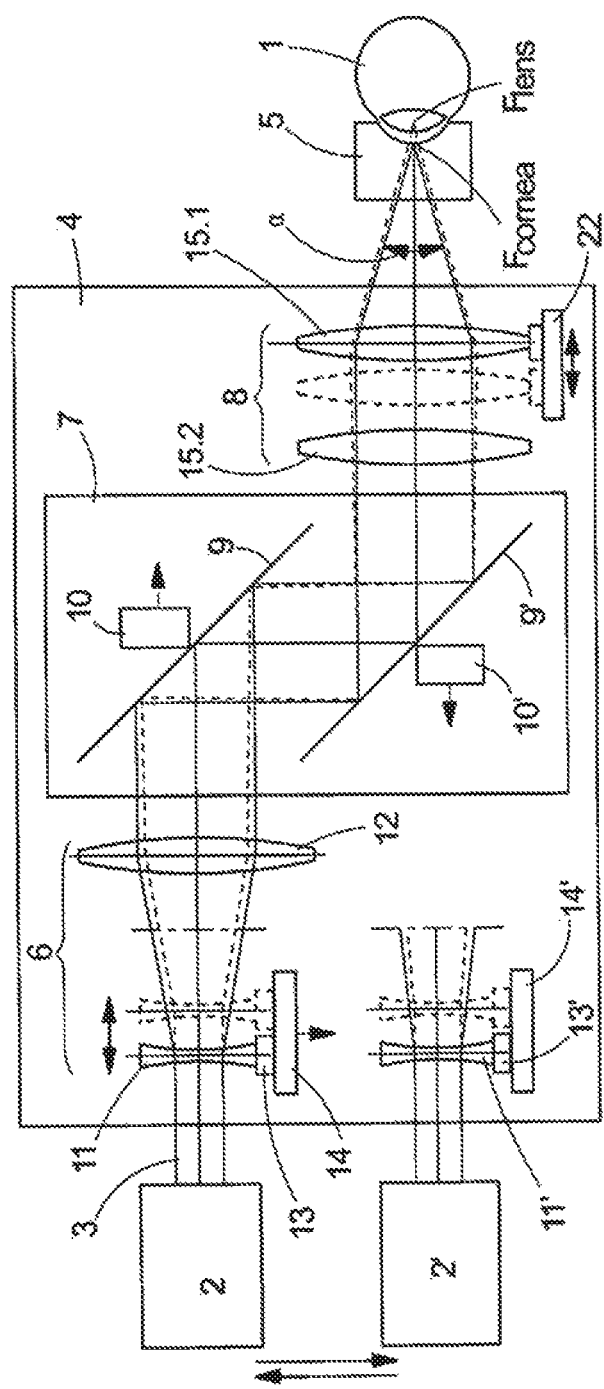
FIG. 3 is a schematic diagram of the invented instrument for surgical laser examination and treatment of the eye in a first preferred embodiment.

FIG. 3 is a diagram of the invented instrument in a first preferred embodiment. Here, the objective 8 consists of two lens groups 15.1 and 15.2, which are shown as single lenses for the sake of clarity. The lens group 15.2 is in a fixed position along the beam path, whereas the lens group 15.1 is arranged to as to be movable along the optical axis and, for this purpose, is coupled via with a straight-line guide with, e.g., a linear drive 22, which, triggered by a control device (not shown), effects the movement.

The distance through which the lens group 15.1 is moved, while principally depending on the control signal, is preferably defined by two limit positions. In FIG. 3, a first limit position is indicated by the lens group 15.1 drawn in solid lines, whereas the second limit position is drawn in broken lines.

This invariable moving distance defined by the limit positions corresponds to the shifting of the focus position from the region of the cornea to the region of the lens of the eye and vice versa. As a result, the arrangement according to the invention can be used for the examination and treatment of both the cornea and the lens of the eye. As patients' eyes naturally differ in size, one embodiment of the invention provides for the moving distance to be variable according to the eye 1. In this case there is only one fixed stop for cornea work, and a continuously variable limit for eye lens work.

If the lens group 15.1 is in the first limit position, the focus position can be varied in Z direction by means of lens 11 and in X and Y direction by means of deflecting device 7 in such a way that this allows targeting of all desired targets within the region of the lens of the eye but not beyond this region. Analogously this also applies to the second limit position and, thus, to the possibility of targeting all desired targets within the region of the cornea.

The movement of lens group 15.1 between the two limit positions, or the release of instructions for such movement, corresponds to the switching of the invented instrument between two operating modes, with the instrument being usable for the examination and treatment of the lens of the eye in one operating mode, and for the examination and treatment of the cornea in the other.

In an extended embodiment, an optional facility is provided to vary the beam diameter 3' in order to adapt the aperture angle α on the side of the eye 1 to the operating mode employed. If the ratio of the amounts of the refractive powers of lens 11 and the collecting lens 12 is decreased, the diameter of the parallel beam 3' emerging from the collecting lens 12 will decrease, too, and, as a result, so will the aperture angle α on the side of the eye 1. A smaller aperture angle α is advantageous for focus positioning on or in the lens of the eye, as in front (upstream) of the lens of the eye there is the pupil as a restricting aperture for the convergent beam 3 entering the lens of the eye, which improves the optical correction.

As shown in FIG. 3, a change of the ratio of the refractive powers in the optical system 6, and, thus, of the diameter of the beam 3' is effected by exchanging several—here, for example, two—lenses 11 and 11' with differing refractive powers against one another. Either, one may exchange merely lenses 11 and 11' against one another, or the assembly consisting of radiation source 2, lens 11, lens holder 13 and linear drive 14 against an assembly consisting of radiation source 2', lens 11', lens holder 13' and linear drive 14'.

Optionally, lens 11 and collecting lens 12 may be exchanged together as a pair to achieve the same effect.

The change of the divergence angle may, in a first version, be positively coupled with switching between the operating modes, i.e., be effected automatically, or, in alternative second version, as a function of the size of the eye to be examined or treated. As a measure of the eye's size one may use, e.g., the depth of the eye's anterior chamber, which is separately ascertained prior to the start of an examination. In the first place, it is the movement of lens 15.1 that is derived from the measurement of the eye. The adaptation of the diameter of the beam 3' via the ratio of refractive indices within the optical system 6 may be effected automatically in connection with switching between the operating modes.

Figure 4:
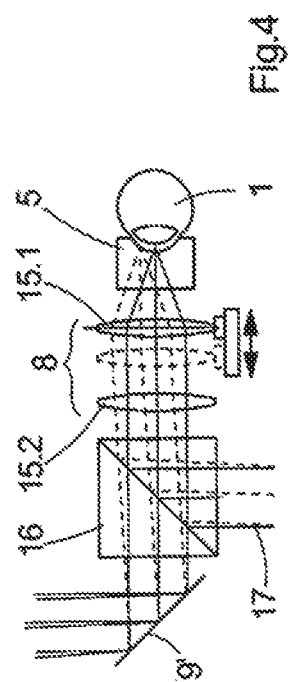
FIG. 4 depicts a variation of the embodiment shown in FIG. 3, featuring a beamsplitter for deflecting the observation beam towards a viewing tube with an eyepiece, or towards a camera.

FIG. 4 shows a variation of the arrangement shown in FIG. 3, with a beamsplitter 16 arranged between the deflecting device 7 and the objective 8. By application of the beamsplitter 16, part of the light coming from the eye and shaped by the objective 8 into an observation beam 17 is coupled out and deflected towards a viewing tube (not shown) with an eyepiece, or towards a camera (not shown either), so that the eye detail being examined or treated can be observed.

Figure 5:
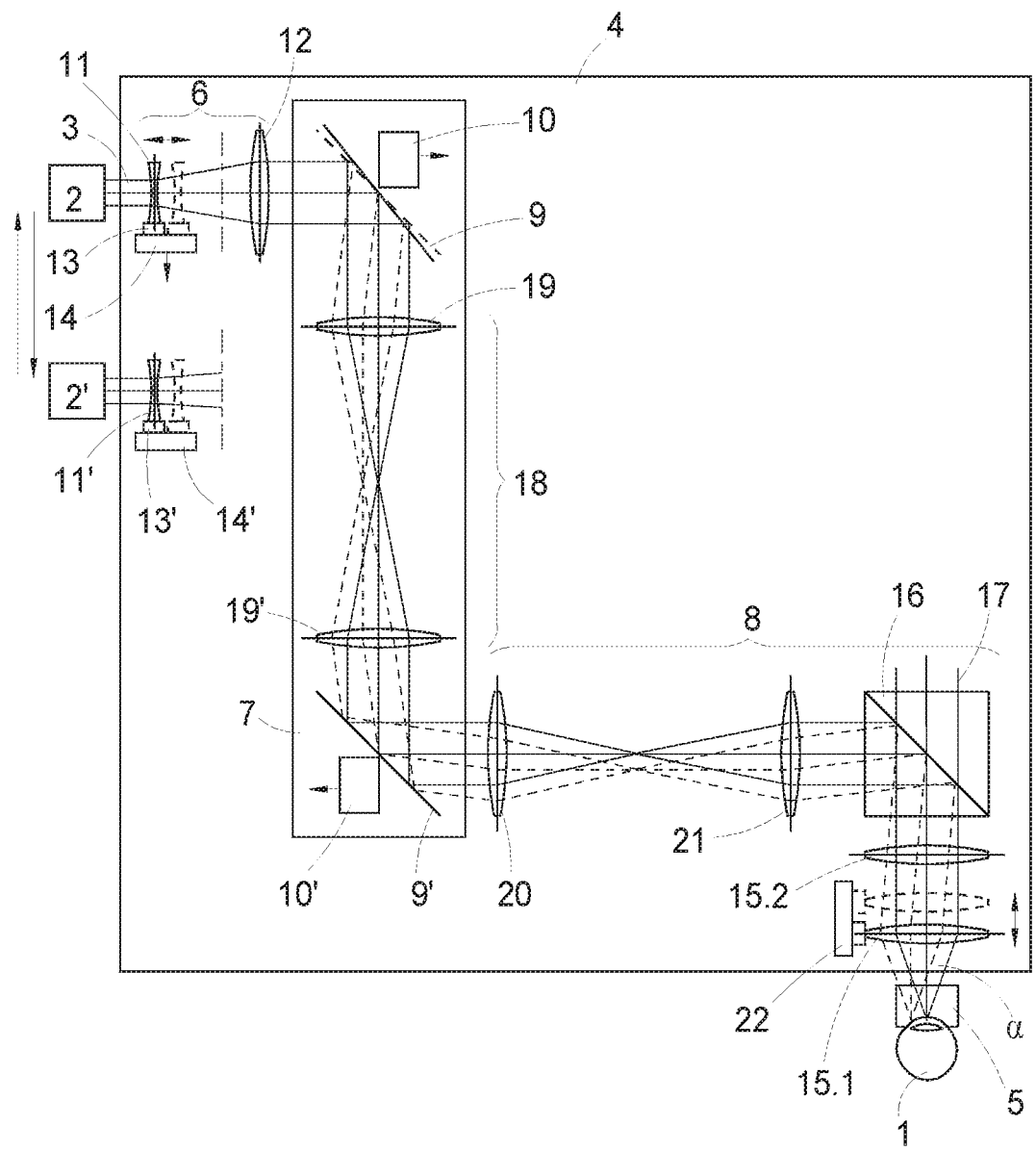
FIG. 5 is a schematic diagram of the invented instrument for surgical laser examination and treatment of the eye in a second preferred embodiment.

FIG. 5 shows another preferred embodiment of the invention. In FIG. 5, components like those in the preceding examples have like reference numbers.

Here, arranged between mirrors 9 and 9' in the beam path is an optical pupil system 18. It comprises two collecting lenses 19 and 19', which project the beam 3 deflected by mirror 9 onto mirror 9', with an intermediate real image being produced in the air between the collecting lenses 19 and 19'. In this way, a fixed position of the pupil results, which makes an optically favorable design of the objective 8 possible. Moreover, due to each of the mirrors 9 and 9' being imaged in the other, mirror 9' can be kept small. The mirrors 9 and 9' may be, e.g., of elliptical shape.

In this embodiment of the invention, the objective 8 is a multiple assembly, comprising an entrance group of lenses 20, a tube lens 21, and the lens groups 15.1 and 15.2.

The beam 3 laterally deflected by the deflecting device 7 enters the entrance group of lenses 20, which focuses it to form an intermediate real image. The tube lens 21 projects the intermediate image to infinity. A beamsplitter 16 deflects the beam 3 to the lens groups 15.1 and 15.2.

Changing the focus position in the coordinate directions X, Y and Z is effected as described in the preceding embodiment example. The same applies to the switching between the two operating modes by moving the lens group 15.1 between two limit positions, with the instrument being configured for the examination and treatment of the lens of the eye in one mode, and for the examination and treatment of the cornea in the other.

Advantageously, all optical components are designed in such a way that the intermediate real images are situated in air, so that high-intensity laser radiation cannot cause any optical breakdown in optical components.

In all embodiments of the invention, the radiation source 2, the optical entrance system 6 and the objective 8 are designed for the beam 3 to have a diameter of less than 5 micrometers at the focus. Preferably, the objective 8 has an aperture greater than 0.35.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

LIST OF REFERENCE NUMBERS 1 eye
2 radiation source
3 beam
4 scanning device
5 contact glass
6 optical entrance system
7 deflecting device
8 objective
9, 9' mirrors
10, 10' actuators
11 first lens
12 collecting lens
13 lens holder
14 linear drive
15.1, 15.2 lens groups
16 beamsplitter
17 observation beam
18 optical pupil system
19, 19' collecting lenses
20 entrance group of lenses
21 tube lens
22 linear drive

The invention claimed is:

1. A method for the application of laser radiation in an eye, including for examination and/or surgical laser treatment of the eye, the method comprising:
   applying laser radiation from a femtosecond laser;
   directing the laser radiation through an optical entrance system and an objective from which a beam emerges that is focused in a direction of the eye;
   arranging optical assemblies in front of the objective as seen in a beam direction and in operative connection with the objective;
   selectively varying a focus position in coordinate directions X, Y and Z within a region of the eye;

varying an aperture angle α on a side of the objective facing the eye by varying a refractive power ratio within the optical entrance system and, thus, varying a diameter of a beam emerging from the optical entrance system such that the aperture angle α is smaller when the focus is positioned in a region inside the eye than when the focus is positioned in a region of the cornea.

2. The method as claimed in claim 1, further comprising:

locating in front of the objective, a lens of negative refractive power that is part of the optical entrance system and that is movable along the beam direction, the movement of which varies the focus position in the coordinate direction Z; and locating a deflecting device in front of the objective that varies the focus position in the coordinate directions X and Y, and locating the deflecting device between the lens and the objective.

3. The method as claimed claim 2, further comprising locating a collecting lens behind the lens of negative refractive power as seen in the beam direction as part of the optical entrance system.

4. The method as claimed claim 3, further comprising operably coupling the lens of negative refractive power with a linear drive.

5. The method as claimed in claim 3, further comprising making a pair of the lens of negative refractive power and the collecting lens one among several pairs which are exchangeable with one another to effect the variation of the refractive power ratio within the optical entrance system.

6. The method as claimed in claim 2, further comprising making the lens of negative refractive power one among several lenses which are exchangeable against one another to effect the variation of the refractive power ratio within the optical entrance system.

7. The method as claimed in claim 2, further comprising making an assembly comprising the radiation source and the negative-power lens exchangeable with assemblies comprising lenses with different negative powers.

8. The method as claimed in claim 2, further comprising arranging two mirrors at a distance from each other and such that the two mirrors can be tilted relative to each other to form the deflecting device.

9. The method as claimed in claim 8, further comprising arranging an optical pupil system comprising two collecting lenses between the mirrors.

10. The method as claimed in claim 2, further comprising arranging a beamsplitter that couples out a partial beam directed at an eyepiece or a camera in a beam path between a deflecting device and the objective.

11. The method as claimed in claim 1, further comprising coupling the variation of the aperture angle α on the side of the objective facing the eye with shifting of a focus position from the region of the cornea to the region of a lens of the eye and vice versa.

* * * * *